United States Patent [19]

Spies

[11] Patent Number: 4,929,898
[45] Date of Patent: May 29, 1990

[54] TRANSIENT ELECTROMAGNETIC METHOD FOR DETECTING IRREGULARITIES ON CONDUCTIVE CONTAINERS

[75] Inventor: Brian R. Spies, McKinney, Tex.

[73] Assignee: Atlantic Richfield, Los Angeles, Calif.

[21] Appl. No.: 291,632

[22] Filed: Dec. 29, 1988

Related U.S. Application Data

[63] Continuation-in-part of Ser. No. 134,368, Dec. 17, 1987, Pat. No. 4,843,320.

[51] Int. Cl.$^5$ .................... G01N 27/90; G01R 33/12; G01B 7/10
[52] U.S. Cl. .................................. 324/242; 324/225; 324/229
[58] Field of Search ................ 324/229, 230, 236–243, 324/336, 71.1, 65 CR, 225; 367/68, 71

[56] References Cited

U.S. PATENT DOCUMENTS

| | | | |
|---|---|---|---|
| 3,875,502 | 4/1975 | Neumaier | 324/242 X |
| 4,339,720 | 7/1982 | Halverson | 324/362 |
| 4,417,210 | 11/1983 | Rocroi et al. | 324/336 |
| 4,535,293 | 8/1985 | Rocroi et al. | 324/336 |
| 4,631,533 | 12/1986 | Mark, Jr. | 324/233 X |
| 4,677,379 | 6/1987 | Arnaud et al. | 324/242 |
| 4,692,701 | 9/1987 | Dundas et al. | 324/240 |
| 4,839,593 | 6/1989 | Spies | 324/240 |
| 4,843,319 | 6/1989 | Lara | 324/240 |
| 4,843,320 | 6/1989 | Spies | 324/240 |

Primary Examiner—Gerard R. Strecker
Attorney, Agent, or Firm—Geoffrey A. Mantooth

[57] ABSTRACT

A transient electromagnetic method for detecting irregularities on container walls by measuring wall thickness. The method utilizes a transmitting antenna and a separate receiving antenna arranged in a loop-loop configuration. The transmitting antenna induces current into the container wall and the receiving antenna and the receiver detect the decay of the induced current, which is then analyzed to detect wall thickness. A receiving antenna array of many receiving antennas is used to increase the spatial resolution. Simultaneous measurement of the induced current by the receiving antennas reduces noise that is coherent across the array. Use of a noise antenna located so as to be unaffected by the transmitting antenna further reduces noise. The received signal from the receiving antenna array is displayed on a two-dimensional display in a spatial arrangement that corresponds to the spatial arrangement of the receiving antennas. The display can be scrolled over the time range of the received signals to produce a moving image, so that irregular areas can be more easily detected than with a static display.

24 Claims, 9 Drawing Sheets

TRANSIENT ELECTROMAGNETIC METHOD FOR DETECTING IRREGULARITIES ON CONDUCTIVE CONTAINERS

This is a continuation-in-part of application Ser. No. 07/134,368, filed Dec. 17, 1987 now U.S. Pat. No. 4,843,320, issued June 27, 1989.

FIELD OF THE INVENTION

The present invention relates to a non-destructive method for detecting irregularities on electrically conductive containers such as pipelines, storage vessels, pressure vessels and the like.

BACKGROUND OF THE INVENTION

Pipelines used to transport petroleum fluids such as crude oil and natural gas are commonly wrapped with a jacket of insulating material. For example, in Alaska and other cold climates, insulation is provided along pipelines to prevent the rapid cooling of oil and gas fluids, thus providing better transportability of these fluids. In refineries, pipelines transporting hot fluids are insulated in order to protect personnel from the high temperatures.

In insulated pipelines, the insulation retains moisture around the outside of the pipeline, which moisture promotes corrosion. Therefore, proper maintenance of insulated pipelines requires their periodic inspection for corrosion and other potential leak sources. However, the insulation, which serves as a thermal barrier, also serves as a barrier to inspection with many prior art inspection techniques. Removal of the insulation for inspection and rewrapping of insulation after inspection is both time consuming and expensive. The inspection process is complicated further on those pipelines covered with a metal jacket over the insulation. The metal jacket is used to keep out moisture. The metal jacket is typically provided in two half portions with each portion having flanges for aiding in the retention of the jacket on the pipeline. The two half portions of the jacket are joined together at the flanges which form seams. Water occasionally enters through the jacket seams and travels through the insulation to the pipe where it causes corrosion.

Prior art methods of detecting pipeline corrosion have proven inadequate. For example, pigs with corrosion detection equipment can only be used on pipelines that have locations providing access to the interior of the pipeline; many pipelines lack such locations. Ultrasonic detection methods require removal of the metal jacket and insulation, a lengthy and expensive procedure. Radiography detection methods are potentially hazardous and the equipment is cumbersome, requiring impractical or inconvenient adjacent vehicular support. Furthermore, with radiography methods it is often difficult to distinguish between corrosion pits filled with corrosion products and uncorroded portions of pipe walls. What is needed then is a method of detecting corrosion through insulation and the surrounding jacket, and which method can be practiced with portable equipment.

Electromagnetic probing techniques provide such a method for detecting corrosion through insulation. In the prior art, frequency domain electromagnetic probing techniques are used to detect corrosion in aircraft fuel tanks. Frequency domain electromagnetic probing techniques utilize a small number of frequencies and measure magnitude and phase differentials between the transmitted signals and the received signals. However, because frequency domain techniques, as a practical matter, utilize only a small number of frequencies, the amount of information obtained is inherently limited, thus detracting from the accuracy of the techniques. In addition, the induced field must be measured in the presence of a much stronger primary field, thus reducing sensitivity.

I have invented a method for inspecting pipelines and other types of electrically conductive containers, using transient electromagnetic phenomena. The method is described in my U.S. Patent Application Ser. No. 07/134,368, filed Dec. 17, 1987, entitled "METHOD FOR DETECTING CORROSION ON CONDUCTIVE CONTAINERS", of which this application is a continuation-in-part. Transient electromagnetic phenomena are utilized to inspect insulated pipelines without removing the insulation or the metal jacketing. This continuation-in-part application describes improvements to the method of inspecting containers such as pipelines which improvements allow increased spatial resolution and increased speed of data acquisition and thus inspection time. This application also describes a method of displaying the data received from the induced current decay in the container walls, which method results in improvements in data analysis.

SUMMARY OF THE INVENTION

It is an object of the present continuation-in-part invention to provide an improved method for detecting corrosion in conductive containers using transient electromagnetic phenomena.

The method of the present continuation-in-part invention detects irregularities on conductive walls of container means by providing transmitting antenna means connected with transmitter means, and receiving antenna means connected with receiver means. The transmitting antenna means is placed in proximity to that portion of the containers means wall which is to be investigated for wall loss, and the receiving antenna means in proximity to the container means wall and near the transmitting antenna means. The transmitting antenna means is physically separate from the receiving antenna means so as to form a separated loop or loop-loop antenna configuration. An abruptly changing current is provided to the transmitting antenna means from the transmitter means so as to induce current into the container means wall portion, and the presence of and the decay of the induced current is detected by the receiving antenna means and the receiver means which produces a received signal. The intermediate and late time ranges of the received signal are examined and compared to the intermediate and late time ranges of a reference received signal. The reference received signal is obtained from a reference container means wall portion of known wall thickness. The decay of the received signal gives an indication of the thickness of the investigated container means wall portion and the presence or absence of irregularities on the investigated container means wall portion can be determined.

With the loop-loop configuration, the separated antennas can be positioned in accordance with pipeline geometrical considerations. Furthermore, the receiving antenna receives only a portion of the induced current, which portion has directional characteristics instead of the omnidirectional characteristics of the induced current received by the coincident receiving antenna.

In one aspect, the method of the present continuation-in-part invention uses receiving antenna means that includes many receiving antennas. The receiving antenna means and the receiver means detect the induced current which has been induced in the container means wall portion by the transmitting antenna means. The receiving antennas and the receiver means produce many received signals which are obtained simultaneously. The individual received signals are divided into samples of time such that the respective samples of time of each received signal correspond to the respective samples of time of the other received signals. A two-dimensional display is created on a display means, for a sample of time, by displaying the respective corresponding time sample of each of the received signals in a spatial arrangement on the display means. The spatial arrangement of the received signals corresponds to the spatial arrangement of the receiving antennas on the container means wall portion.

By simultaneously measuring the induced current in the container means wall portion with the receiving antennas, spatial resolution is greatly enhanced. This is because most noise sources (for example power line noise, sferics, motion-induced noise) picked up during TEMP data acquisition are coherent across the receiving antenna array. Thus, for any given time sample, the noise does not affect the induced current as seen by one receiving antenna any more or less than it affects the induced current as seen by the other receiving antennas. Instead, the noise raises or lowers the background (or dc) level of the entire array of received signals for a given time sample. The use of many receiving antennas also increases the speed of data acquisition.

From one time sample to another, resolution (temporal resolution) can be increased by subtracting a noise signal. The noise signal is obtained from a noise antenna which is placed along the container means wall at a distance from the transmitting antenna means such that the noise antenna is unaffected by the transmitting antenna means. The noise signal is measured simultaneously with the other received signals. The noise signal is subtracted from each of the received signals. The noise signal is coherent with the noise present in the receiving antennas because the spatial changes in the noise present at the receiving antenna array and the noise antenna are negligible and because the noise signal is measured simultaneously with the received signals.

In another aspect, the transmitting antenna means includes a loop antenna which encompasses an interior space. The receiving antenna means is placed within the transmitting means interior space. The transmitting antenna means is geometrically configured to produce an induced current which produces an electromagnetic field that is relatively uniform over a portion of the interior space of the transmitting antenna means. In another aspect, the transmitting antenna means includes a loop antenna with an interior space, wherein the container means wall is located within the interior space.

In another aspect, the two-dimensional displays are displayed on the display means in a consecutive temporal arrangement. This method displays corroded areas over the time range of the received signals. The corroded areas appear to grow and shrink with time as the screens are scrolled in time on the display. Such change in the corroded areas is easier to visually detect and makes possible the detection of small or weak areas of corrosion that would otherwise escape visual detection by static display means.

DESCRIPTION OF PREFERRED EMBODIMENTS (FIGS. 1-8d)

Figure 1:
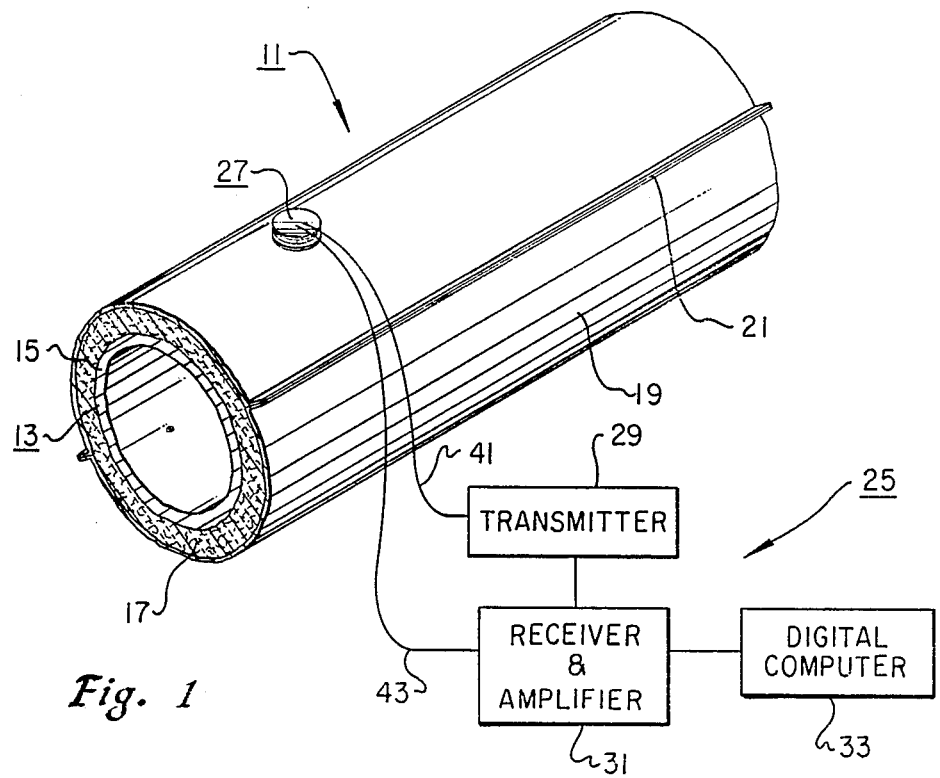
FIG 1 is a schematic diagram showing a typical situation in which the method for detecting corrosion in a container in accordance with a preferred embodiment of the present invention can be practiced, together with typical testing apparatus.
Figure 2:
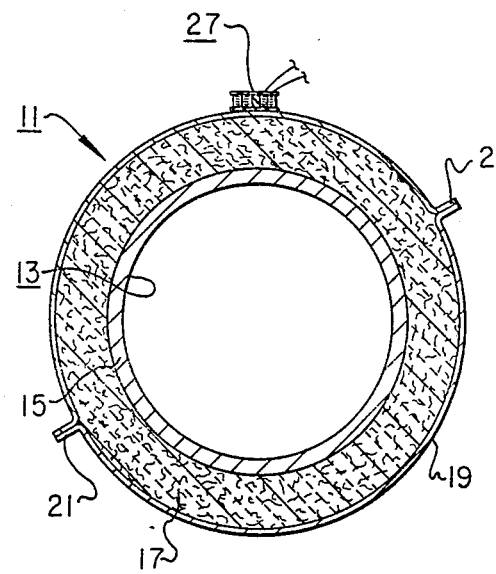
FIG. 2 is a schematic diagram showing a transverse cross-section of the pipeline of FIG. 1.
Figure 3:
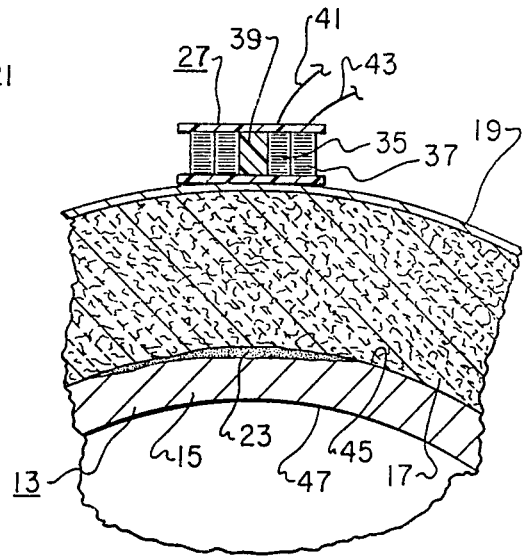
FIG. 3 is a schematic cross-sectional view showing the antenna means of FIG. 2 in detail.

In FIGS. 1-3 there is schematically shown a typical situation in which the method of detecting corrosion in electrically conductive containers 11 can be practiced, together with typical detecting apparatus 25. The method of the present invention utilizes transient electromagnetic probing (TEMP) to detect corrosion.

The conductive container shown in FIGS. 1-3 is a portion of a pipeline 11, which is of course made up of a plurality of individual pipes 13. The pipes 13 have a diameter and the pipe walls 15 have a thickness. The pipe walls 15 are made up of an electrically conductive material such as steel.

In Alaska's Prudhoe Bay region, pipelines wrapped with insulating material 17 are used to transport oil and gas fluids. The insulation 17 is provided to prevent rapid cooling of the oil and gas fluids in the pipeline and thus provide better transportability of these fluids in the pipeline. In refineries, pipelines and vessels are commonly wrapped with insulation as a safety measure in protecting personnel from high temperatures. The insulation 17 on pipelines is typically a thermoplastic foam such as polystyrene, and has a radial thickness. Surrounding the insulation 17 is a metal jacket 19 which is provided to keep out moisture. The jacket 19 has a thickness which is much less than the thickness of the pipe wall. The metal jacket 19 has two half portions that extend longitudinally along the pipeline. Each jacket half portion has seam means in the form of flanges 21 that extend radially outward. When the jacket half portions are assembled onto the pipeline, the respective flanges 21 abut one another to form seams. The half portions are retained in place on a pipeline by securing the respective flanges together with suitable means.

In FIG. 3, the pipe wall 15 is shown to have a corrosion pit 23 adjacent to the insulation. The corrosion acts to reduce the thickness of the pipe wall, wherein it forms the pit and fills the pit with corrosion products. The corrosion that has pitted the pipe wall is caused by water that has entered the insulation between the jacket flanges 21.

Detecting apparatus 25 is provided near that portion of the pipe wall which is to be tested for corrosion and includes antenna means 27, a transmitter 29, a receiver and amplifier 31, and a digital computer 33.

The antenna means 27 include a transmitting antenna coil 35, a receiving antenna coil 37 and core means 39. In the preferred embodiment, the transmitting and receiving antenna coils 35, 37 are wound onto the same core means 39, an arrangement which is hereinafter referred to as coincident (see FIG. 3). The core means 39, which is in the shape of a spool, is made of a nonmagnetic and non-conductive material such as plastic. The number of turns of the transmitting antenna coil are kept to a minimum to minimize the inductance of the transmitting antenna and to provide for an abrupt switching off of the transmitting antenna coil. In the preferred embodiment, the transmitting antenna coil 35 is made up of 120 turns of 20 to 24 gauge wire. The receiving antenna coil 37 is made up of 400 turns of 34 to 40 gauge wire. The transmitting and receiving antenna coils 35, 37 are connected to the transmitter 29 and receiver 31 by respective pairs of wires 41, 43.

The transmitter 29 which is conventional, generates a train of pulses having magnitudes of 1 to 5 amps. As discussed in more detail below, a plurality of pulses are transmitted for each location of the antenna means 27 for data enhancement purposes. The pulses have abrupt fall times on the order of 10 to 100 microseconds. The pulses of the transmitter pulse train alternate polarity to eliminate dc bias in the instrumentation. The duration of each pulse is sufficiently long to stabilize the pulse magnitude so that there are no induced currents in the pipe wall before the end of the pulse. The transmitter 29 repeats the pulses at a repetition rate that allows all of the necessary data to be obtained for each pulse. For example, a thick pipe wall requires more time to obtain data than does a thinner pipe wall because the induced current takes longer to diffuse in the thick pipe wall. Thus, the repetition rate of pulses will typically be slower for thick pipe walls than for thinner pipe walls.

The receiver and amplifier 31 is a broad band instrument with a wide (5 or 6 orders of magnitude) dynamic range. The receiver 31, which has an A/D converter, samples the signal at a constant rate and integrates the signal over a time window or channel. The duration of the time windows increases with time. The transmitter 29 and the receiver and amplifier 31 are conventional. In practice it has been found that the SIROTEM transmitter, receiver and amplifier unit manufactured by Geoex Pty. Ltd. of Adelaide, Australia, works well. The battery operated SIROTEM unit is portable, a characteristic which allows ease of use when surveying pipelines in the field.

The digital computer 33 is a conventional portable computer with sufficient memory capacity to record the data.

The method of detecting corrosion on a conductive container of the present invention will now be described. As mentioned earlier, the method of the present invention utilizes transient electromagnetic probing (TEMP). TEMP allows the remote probing of a conductor by inducing a current into the conductor and then analyzing the decay of the current.

First, the antenna means 27 is placed on the jacket 19 so as to be in proximity with the near surface 45 of the portion of the pipeline 11 that is to be investigated. Suitable means (not shown) are used to secure the antenna means 27 in position so as to minimize any motion of the antenna means over the investigated pipe wall portion. The transmitting antenna coil 35 is then energized by the transmitter 29 with a pulse. As described above, the transmitting antenna coil 35 is energized for a sufficient period of time to stabilize the pulse magnitude, thereby insuring no eddy currents are induced into the pipeline 11. Then, the transmitting coil 35 is abruptly deenergized by the transmitter by having the pulse fall off rapidly to zero magnitude. This abrupt deenergization of the transmitting antenna coil 35 induces eddy currents into the conductors located near the coil; namely the jacket 19 and the pipe wall 15. The eddy currents, which decay and diffuse away from the antenna means 27 inside of the respective conductors, create a magnetic field that is detected as a time-varying voltage in the receiving antenna coil 37. As soon as the transmitting antenna coil is deenergized, the receiver 31 is then switched on. The receiving antenna coil 37 detects the presence of and the decay of the induced eddy currents in the conductor. The eddy currents are gradually dissipated within the conductors by resistive heat losses. The rate of diffusion is dependent on the conductivity and thickness of the conductor. The receiver 31 samples the signal as detected by the receiving antenna coil 37, whereupon it is amplified by a suitable level and sent to the digital computer 33 for storage and processing. The receiver 31 measures the signal from the time the eddy currents are first induced into the conductors until the signal becomes indistinguishable from noise. The level of noise is reduced by minimizing any motion of the receiving antenna coil 37 relative to the conductors. The received signal is unprocessed data and forms a record in the computer 33 of the decay of the induced currents in the conductors. The transmitting and receiving procedure is repeated many times with the antenna means 27 in the same location to increase the signal-to-noise ratio.

Figure 4:
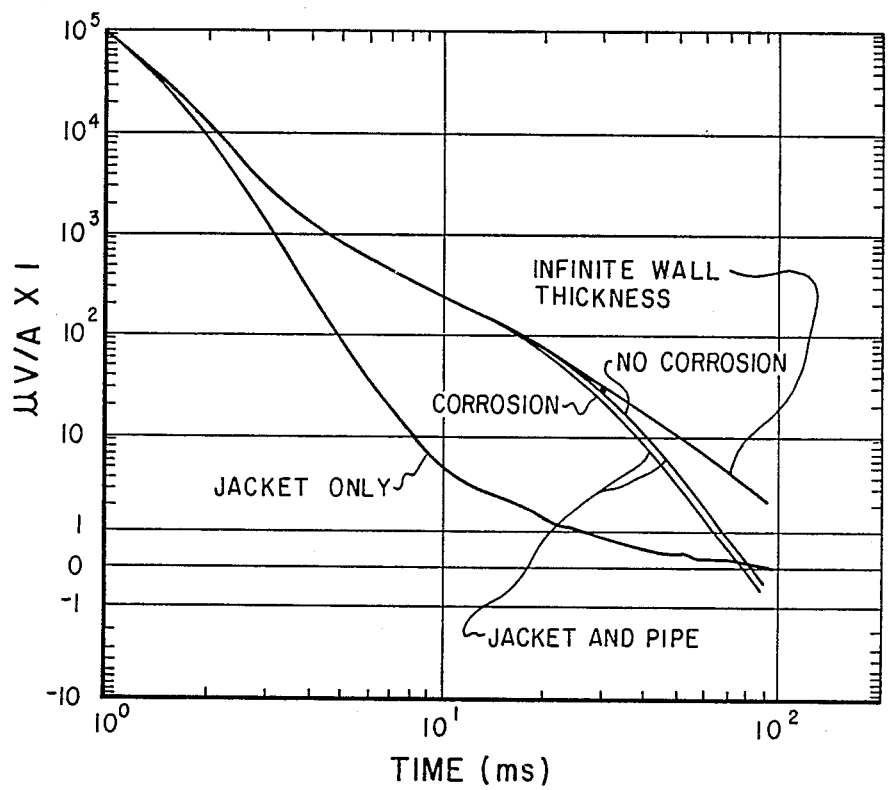
FIG. 4 is a graph showing the time domain response curves of various conductors, obtained by the transient electromagnetic probing (TEMP) method of the present invention.

The data is then processed by computer data processing means into a suitable format for interpretation. The first steps in the processing of the data involve the normalization of the received signals and the summing and averaging of the received signals. Because the transmitter 29 in the preferred embodiment is battery operated, the magnitude of the transmitter current is subject to variation. The effects of variation in magnitude in the data are removed by normalizing the received voltage to the transmitted current. The summing and averaging of the received signals for a particular antenna means location serves to increase the signal-to-noise ratio. In particularly noisy environments, as an alternative to summing and averaging, selective stacking can be used to eliminate noisy transients. The result of this initial data processing is a time-varying response curve such as shown in FIG. 4. (FIG. 4 illustrates response curves for various conductors.)

The response curves may be interpreted in accordance with methods which will now be described, with reference to FIGS. 4–8d. Referring in particular to FIG. 4, the presence or absence of corrosion on a conductor wall is inferred by examining the shape of the various response curves which have been taken over the area of interest. The shape of each response curve depends in part on the thickness of the conductor wall. For example, the magnitude of the response curve of an infinitely thick conductor wall decays at a fairly even rate (on a log-log graph), resulting in a fairly straight response curve, whereas the response curve of a conductor having a finite wall thickness begins to break at some point into a more pronounced downward direction than before and decays at a faster rate. This breaking phenomenon is attributed to the induced currents diffusing to and reaching the far surface 47 of the conductor wall. Response curves for thin conductor walls break at earlier times than do response curves for thicker conductor walls.

Because corrosion reduces the thickness of a conductor wall, the presence or absence of corrosion can be inferred by comparing the shape of the response curve for the investigated pipe wall portion to the shape of the response curve for an uncorroded portion of the same type of pipe. For example, in FIG. 4, the two response curves labeled "corrosion" and "no corrosion" are taken from the same pipe. The "no corrosion" response curve is taken from an uncorroded portion of the pipe and is used as a reference, while the "corrosion" response curve is taken from a different portion of the same pipe, which different portion has a pit to simulate corrosion (with the antenna means located at the same distance from the pipe wall, for both response curves). At about 17 ms (milliseconds), the "corrosion" response curve breaks into a more pronounced downward direction and begins to decay at a faster rate than before. The "corrosion" break point occurs at an earlier time than does the "no corrosion" break point (at about 25 ms), indicating that the conductor wall represented by the "corrosion" response curve is thinner than the conductor wall represented by the "no corrosion" response curve.

Figure 5:
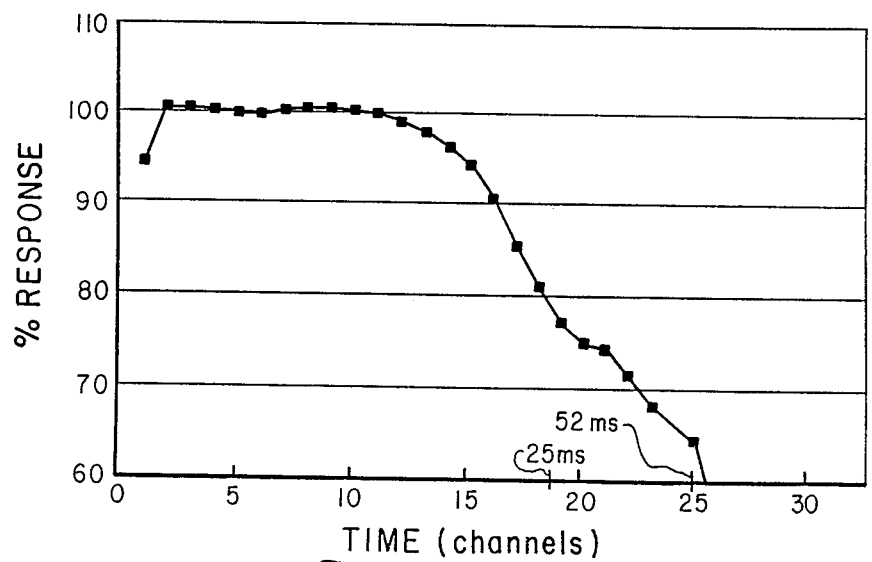
FIG. 5 is a graph of the response curve of a pit in a pipe wall, with the response curve obtained by computing the ratio of the "corrosion" to the "no corrosion" response curves of FIG. 4.

Referring now to FIG. 5, the "corrosion" and "no corrosion" response curves of FIG. 4 are compared by plotting the ratio of the two curves as a percent response curve, using the "no corrosion" response curve as a reference. The percent response curve highlights the differences between the "corrosion" and the "no corrosion" response curve. By examining the late time portions of the percent response curve (from about 17–20 ms on, which is about when the "corrosion" response curve of FIG. 4 begins to break sharply downward), one can see that the "corrosion" response curve deviates 20 to 30 percent from the "no corrosion" response curve. This 20 to 30 percent difference clearly indicates a difference in wall thickness between the corroded portion of the pipe and the uncorroded portion of the pipe.

In FIG. 4, the response curve labeled "jacket only" is that taken from the metal jacket 19, without the pipe 13. The "jacket only" response curve decays very rapidly so that by the relatively late time of 20 ms, the jacket 19 contributes very little to the total response. This is because the wall thickness of the jacket is much smaller than the thickness of the pipe wall, so the currents diffuse much more rapidly in the jacket. Thus, for those portions of the "jacket and pipe" response curves that are of interest in locating corrosion (that is the later times), the effect of the jacket can be ignored.

Figure 7:
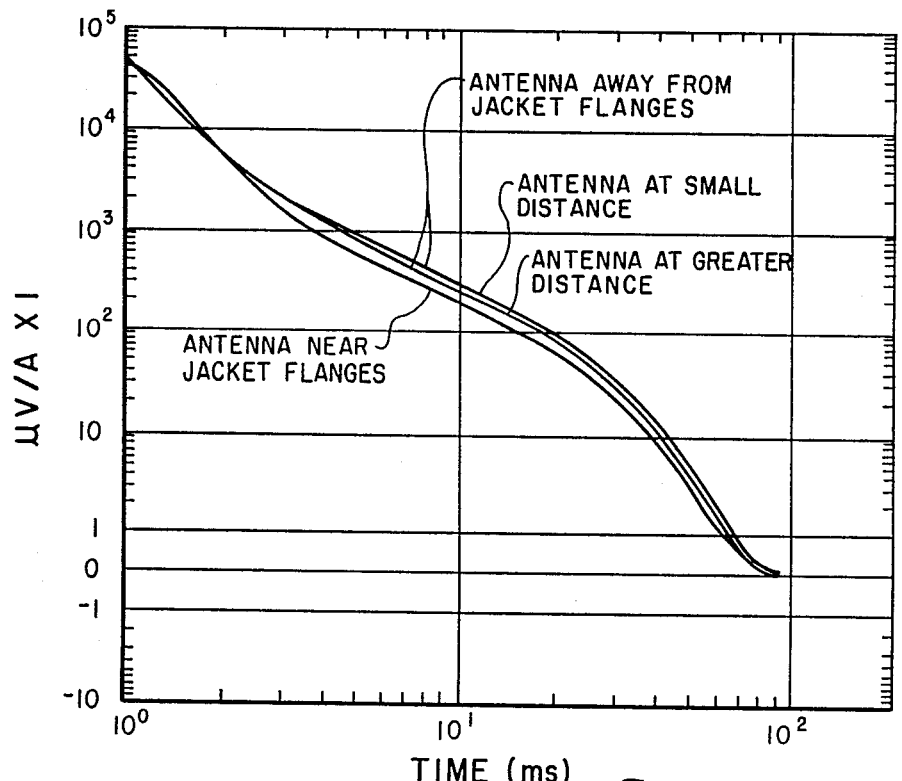
FIG. 7 is a graph showing the effects of the jacket flanges and of variations in antenna means height on time domain responses of pipe walls.

Responses measured near jacket flanges are affected quite strongly by the jacket flanges at all times, as shown in FIG. 7. A response measured near jacket flanges can be corrected to remove the effects of the jacket flanges by normalizing the affected response curve to a reference response curve obtained away from the jacket flanges. As shown in FIG. 7, an effect of the jacket flanges on the response curve is a generally parallel shift in a downward direction in the intermediate and late time ranges (later than about 4 ms). That is to say that in the intermediate and late time ranges, the affected response curve is generally parallel to the reference response curves. The affected response curve is corrected by normalizing the affected response curve to the reference response curve in the intermediate time range.

FIG. 7 also serves to illustrate the effect that variations in distance between the antenna means and the pipe wall at one location on the pipe and between the antenna means and the pipe wall at another location on the pipe can have on responses. Such variations in distance result from non-uniform thicknesses of the insulation between the pipe wall and the jacket. Increasing the distance of the antenna means from the pipe wall causes the magnitude of the response to decrease at intermediate and late times, which decrease in magnitude shows up as a generally parallel shift. The responses can be corrected to remove the effects of variations in distance by normalizing the response curves to a reference response curve obtained with the antenna means at some known distance, in the intermediate time range.

The antenna means 27 gives a reading of the average conductor wall thickness over a search area. The size of the search area depends upon antenna size and the distance of the antenna from the wall, antenna configuration and the duration of the receiver measuring time after each transmitter pulse. The search area of the antenna means increases with larger antenna sizes or with longer measuring times. In the preferred embodiment, the antenna means 27 has a diameter of about 3 inches. For a 10.5 inch diameter pipe with wall thickness ⅜ inches, the search area is about 12 inches in diameter.

Figure 8A:
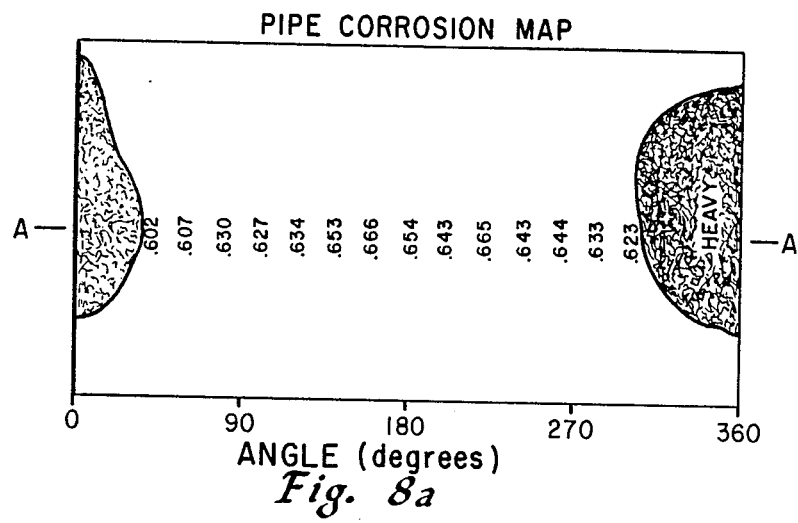
FIG. 8a is a circumferential map of a portion of a pipe showing both the location of corrosion and ultrasonic wall thickness measurements.

In the usual case, the portion of the pipeline that is to be investigated for corrosion is much larger than the search area of the antenna means. Therefore, a typical pipe survey requires the antenna means to be moved to new locations to complete the survey. In FIGS. 8a a through 8d there are shown a corrosion map of a pipe section and corresponding TEMP surveys or profiles along line A—A of the pipe section. In obtaining the TEMP profiles of FIGS. 8b through 8d, the antenna means was positioned at various locations along line A—A. In FIG. 8a, the numbers along line 8a indicate ultrasonic point measurements of the wall thickness (in inches) and the shaded areas indicate heavy corrosion, wherein the thickness of the pipe wall is less than for the unshaded areas. The map shows that the pipe wall along line A—A is thickest around 180 degrees and gets thinner moving towards 0 degrees and 360 degrees.

Figure 8B:
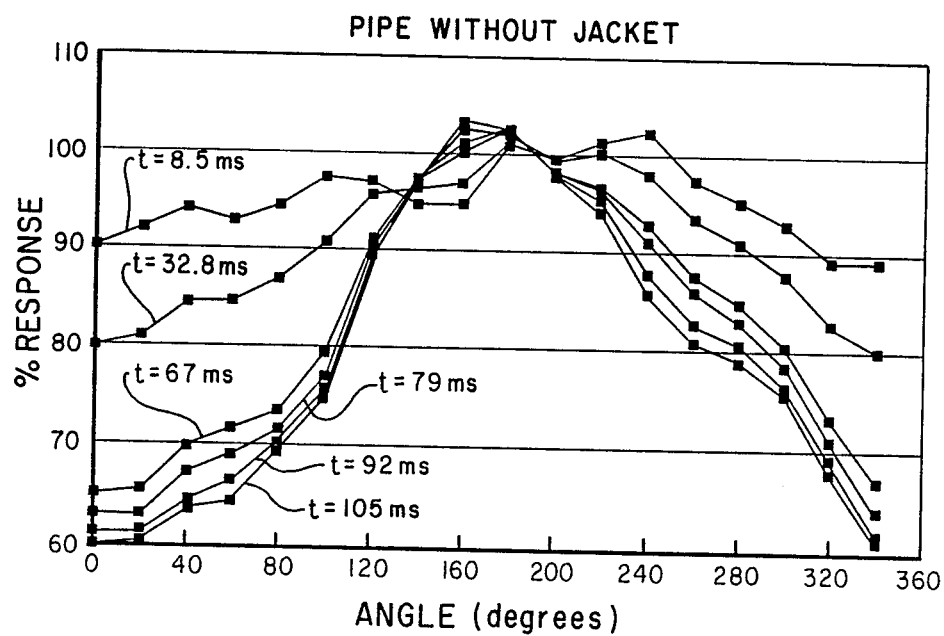
FIG. 8b is a graph showing transverse TEMP profiles of the unjacketed pipe of FIG. 8a, taken along line A—A.

FIG. 8b shows TEMP profiles of the pipe of FIG. 8a along line A—A, without a metal jacket. In FIG. 8b only those values of the response curve at selected discrete instances of time for each antenna means location are plotted. The response curve values at equivalent instances of time are then connected together to form a TEMP profile. Thus, for each antenna means location, the response curve values at time=8.5 ms, 32.8 ms, 67 ms, 79 ms, 92 ms, and 105 ms are plotted, forming respective TEMP profiles of pipe wall thickness. Each TEMP profile is normalized to the TEMP response obtained over the thickest portion of the pipe. As can be seen in FIG. 8b, the TEMP profiles show that in moving away from 180 degrees in either direction (towards 0 degrees and towards 360 degrees) the pipe wall thickness lessens and is thinnest around 0 to 60 degrees and 320 to 360 degrees. The late time TEMP profiles (67 ms and greater) in particular clearly show the reduced wall thickness, corresponding with the pipe corrosion map of FIG. 8a.

Figure 8C:
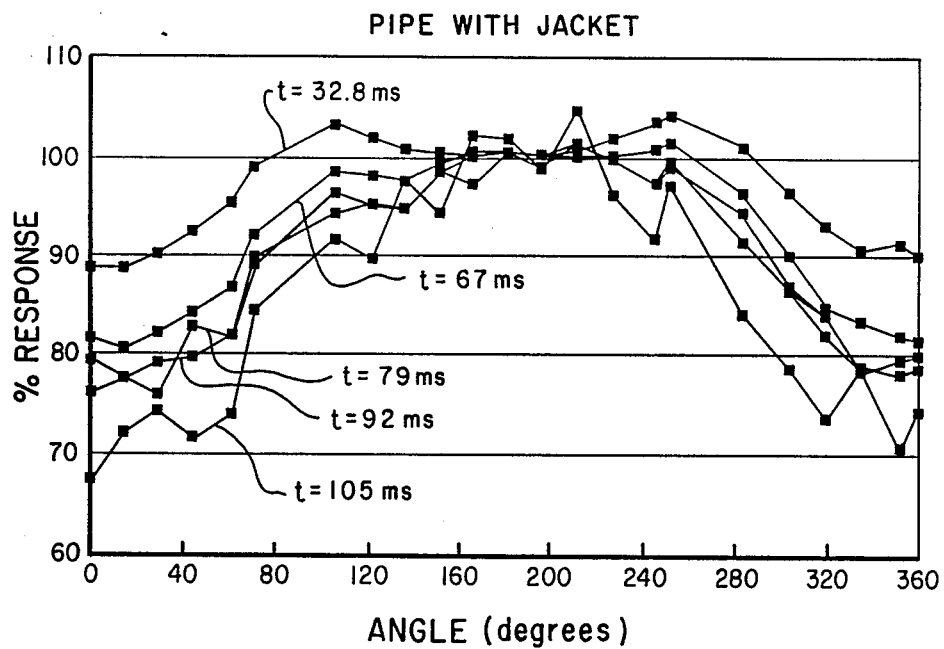
FIG. 8c is a graph showing transverse TEMP profiles of the jacketed pipe of FIG. 8a, taken along line A—A, with the TEMP profiles corrected for the effects of the jacket flanges.

In FIG. 8c, there are shown TEMP profiles of the pipe of FIG. 8a along line A—A, but with a metal jacket. The TEMP profiles of FIG. 8c were obtained in the same manner as the TEMP profiles of FIG. 8a. The jacket flanges, which are located at approximately 95 degrees and 270 degrees, have caused reductions in the amplitudes of the TEMP profile portions near the flanges. The TEMP profiles of FIG. 8c have been corrected to reduce the effects of the jacket flanges by normalizing the responses measured near the jacket flanges to a response measured away from the jacket flanges. The responses are normalized in the intermediate time range (3–6 ms) and the late times (32 ms and greater) are then analyzed. (In FIG. 8d there are shown the TEMP profiles of FIG. 8c before the profiles have been corrected for the effects of the jacket flanges.) There is a good correlation between the TEMP profiles of FIG. 8c and the corrosion map of FIG. 8a. The TEMP profiles of FIG. 8C show that the pipe wall is reduced in thickness around 0 to 60 degrees and 320 to 360 degrees, thus leading to an inference of corrosion at those locations.

FIGS. 8a through 8d illustrate an advantageous difference of the TEMP method over the ultrasonic method. The ultrasonic method makes point measurements, requiring a large number of measurements, whereas the antenna means of the TEMP method has a large search area requiring fewer measurements. While the ultrasonic measurements in FIG. 8a are essentially confined to line A—A, the TEMP measurements encompass portions of the pipe extending for a few inches to either side of line A—A. Furthermore, ultrasonic measurements must be made on the bare pipe, while TEMP measurements can be made on the jacket.

Figure 8D:
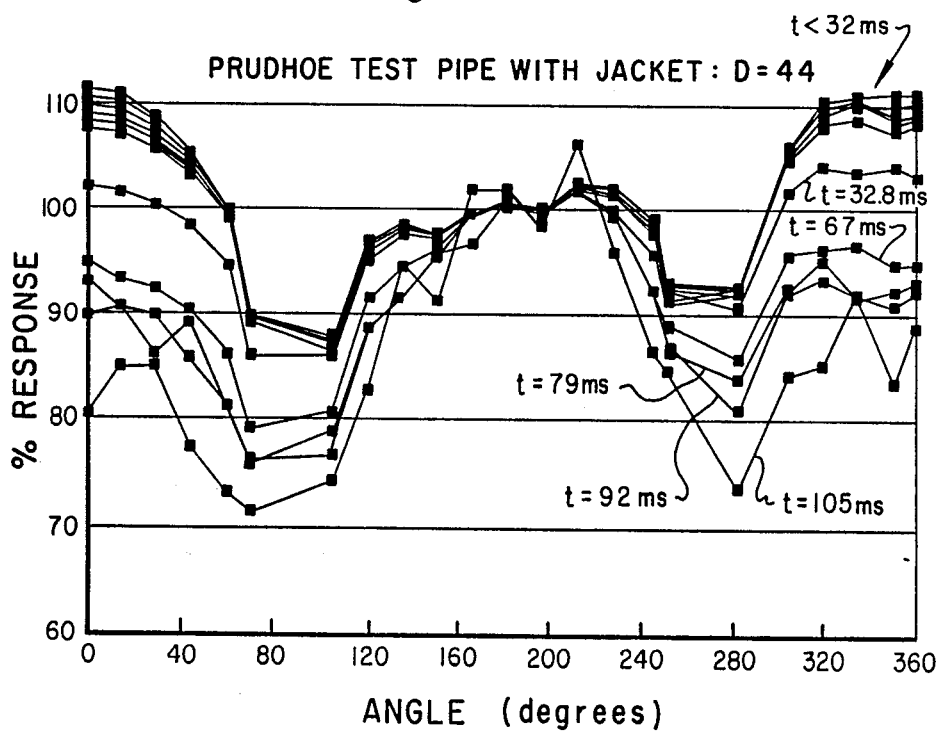
FIG. 8d is a graph showing the same TEMP profiles as in FIG. 8c, but uncorrected for the effects on the jacket flanges.

For TEMP profiles such as are shown in FIGS. 8b–8d, the effects on the responses due to the variations in distance between the antenna means and the pipe wall, which variations are caused by moving the antenna means from one location on the pipe to another location, can be corrected by creating reference response curves with the antenna means placed at a number of known distances from the pipe wall. The intermediate times of the response curves having distance error are then normalized to the intermediate times of the respective reference response curves.

Figure 6:
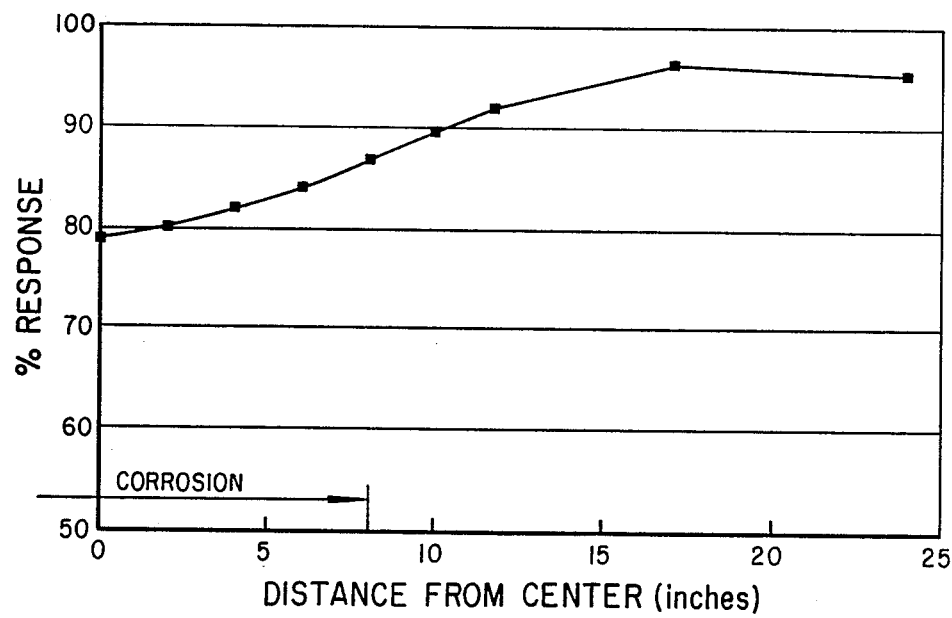
FIG. 6 is a graph showing a longitudinal cross-sectional TEMP profile of the pit of FIG. 5, with the profile being obtained by averaging the late time responses at each antenna means location.

In FIG. 6, there is shown a TEMP profile of the corrosion pit of FIG. 5. The TEMP profile is obtained by moving the antenna means to a plurality of locations and averaging the responses for the 25 to 52 ms time window at each antenna means location. The physical extent of the corrosion pit is indicated at the bottom left corner of the graph, which shows the pit to have a radius of about 8 inches. The TEMP profile of FIG. 6 shows a good correlation to the physical profile. From about 17 inches on, the TEMP profile shows a slight decreased in magnitude due to the induced currents interacting with the nearby pipe end.

Another method of interpretation of the response curves of FIG. 4 involves examining the time at which the far surface 47 of the pipe wall is initially manifested in the response curve. This time is referred to as the "critical time", and is that point where the response curve begins to break into a more pronounced downward direction than before, as discussed hereinbefore (see FIG. 4). The wall thickness of the pipe is proportional to the square root of the critical time. The constant or factor of proportionality is dependent on the geometry and the conductivity of the pipe, and may be determined by making a determination of the critical time of a particular thickness of the pipe.

The method of the present invention can be used to make quantitative measurements of wall thickness, once the instruments and data have been calibrated on pipes of known thickness and conductivity. Once the actual wall thickness of the investigated pipe is known, comparison to the manufactured wall thickness leads to a determination of wall loss due to corrosion on the investigated pipe.

An important aspect of the present invention is the increased accuracy of detection of corrosion on conductive walls over prior art methods. The present invention operates in the time domain rather than in the frequency domain. In the time domain, all the information needed to probe a conductor wall for accurate detection is obtained with one transmitter pulse. Each pulse contains an infinite number of frequencies. With frequency domain methods however, only a few frequencies are used to probe a conductor wall, resulting in a limited amount of information from which wall thickness is to be determined.

Another important aspect of the present invention is the ability to detect corrosion through insulation. Unlike ultrasonic methods, the present invention does not require the expensive and time consuming task of removing non-conductive and even conductive layers that are positioned between the wall of interest and the probe (the antenna means). Furthermore, the present invention has a greatly expanded search area associated with the antenna means, whereas the ultrasonic method produces essentially point measurements. This difference in probe search areas is of particular importance in detecting corrosion in pipeline walls. Corrosion in pipeline walls becomes hazardous when there is wall loss over a relatively large area. Small spots of occasion, while generally a nuisance for potential leakages, do not present the explosive hazard that a large corroded area presents. The TEMP method is more efficient in detecting hazardous pipeline wall loss by giving an average measurement over the antenna means search area.

Although the method of the present invention has been described for use in detecting corrosion on pipelines, the method may also be used to detect corrosion on the electrically conductive walls of other types of container means such as storage vessels and pressure vessels. In addition, the method of the present invention can be used on uninsulated as well as insulated container means.

The antenna means can have the transmitting antenna and receiving antenna configured in arrangements other than the coincident arrangement described herein. One such arrangement has the transmitting antenna separate but coplanar with the receiving antenna. Another arrangement has a plurality of receiving antennas located within a large transmitting antenna loop.

DESCRIPTION OF PREFERRED EMBODIMENTS (FIGS 9-21)

Figure 9:
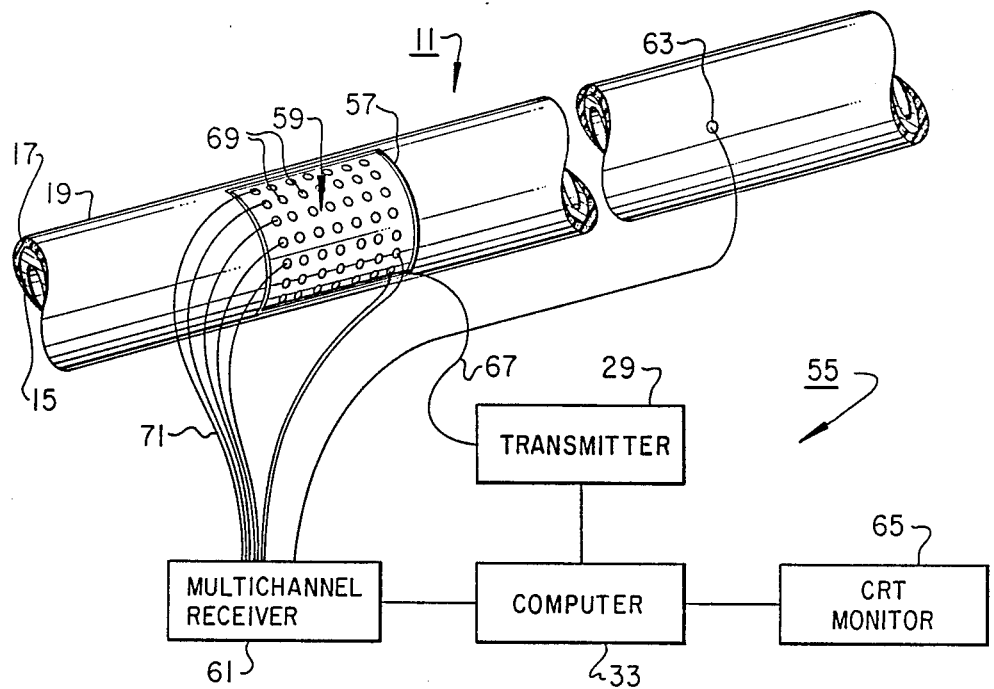
FIG. 9 is a schematic diagram showing a typical situation in which the method for detecting irregularities in a container in accordance with a preferred embodiment of the present continuation-in-part invention can be practiced, together with typical detection apparatus.

In FIG. 9, there is shown a schematic diagram showing a typical situation for practicing the method for detecting irregularities by measuring wall loss on a container of the present continuation-in-part invention in accordance with a preferred embodiment. The wall loss is typically caused by corrosion which can form on the outside or the inside of a container.

The container shown in FIG. 9 is a portion of a pipeline 11. The pipeline is made up of a plurality of individual pipes. The pipes each have a pipe wall 15 which is made up of an electrically conductive material such as steel. In the preferred embodiment, the pipeline is completely encased within an insulating material 17 and a metal jacket 19 that prevents direct access to the outside of the pipe wall by the detecting apparatus 55. The jacket 19 has a thickness which is much less that the thickness of the pipe wall.

The detecting apparatus 55 includes transmitting antenna means 57, the transmitter 29, receiving antenna means 59, receiver means 61, a noise antenna 63, the digital computer 33, and display means 65.

The transmitting antenna means includes a loop antenna 57. The transmitting loop antenna is made up of one or more turns of conductive wire. The transmitting loop antenna 57 is wound around an air core so that the antenna encompasses an interior space. In the preferred embodiment, the transmitting loop antenna 57 is generally rectangular and is formed to follow the curvature of the pipe 13. The transmitting antenna 57 is geometrically configured so that when it is placed onto a pipeline 11, the transmitting antenna will induce a current into the pipe wall 15 that in turn produces a relatively uniform electromagnetic field across a central portion of the transmitting antenna interior space, at intermediate and late times of the induced current decay. The uniformity referred to is spatial uniformity; thus, at any given instant of time, the induced current will appear to be about the same to two or more receiving antennas located within the central portion of the interior space. The central portion is approximately one-half of the area of the interior space, centered at the geometrical center of the interior space. The field produced by the induced current is relatively uniform within about 10%. As will be shown with the detecting apparatus in FIG. 10, a uniform transmitted electromagnetic field is not necessary to the method of the present invention, although a relatively uniform field simplifies the processing of the received signals, and in particular simplifies the normalization of the received signals.

The transmitter 29 is as described above. The transmitting antenna 57 is connected to the transmitter 29 by a pair of wires 67.

The receiving antenna means includes many individual receiving antennas 69 arranged in a predetermined spatial distribution so as to form a receiving antenna array 59. Each of the receiving antennas 69 is electrically separate from the other receiving antennas. Each receiving antenna is made of a coil of wire wound onto a core means. In the preferred embodiment, the core means is made of a nonmagnetic and nonconductive material such as plastic, although a ferromagnetic core could also be used. Each core means has a longitudinal axis. The coil of each receiving antenna is wound circumferentially around the core means. The receiving antennas 69 are arranged in rows and columns so as to form a rectangular array, with the spacing between the rows and columns being approximately equal. The individual antennas are fixed into their spatial distribution relative to one another by suitable means (not shown). The receiving antenna array 59 and the transmitting antenna 57 are sized relative to each other such that the receiving antenna array is completely received by the interior space of the transmitting antenna. The individual receiving antennas 69 should each be about one-half inch to one inch in diameter, in order to allow the placement of a large number of receiving antennas in a small area, thereby increasing the density of the receiving antenna array. The receiving antenna array should contain a large enough number of individual receiving antennas to satisfy resolution requirements. As will be explained in more detail hereinbelow, the higher the number of receiving antennas in the receiving antenna array, the higher the resolution of the container wall that can be obtained with the array. For example, a rectangular array could be made up of ten receiving antennas by twenty receiving antennas.

Each receiving antenna 69 in the array is connected by a respective pair of wires 71 to the receiver 61. (In FIGS. 9 and 10, only some of the wires connecting the receiving antennas to the receiver are shown for clarity.) The receiver 61 is as described above with regard to FIG. 1, with the exception that the receiver 61 has provision for multiple channels. Each channel is connected to a single receiving antenna 69. Each receiver channel has an amplifier and is connected to an analog-to-digital (A/D) converter.

The transmitter 29 and the receiver 61 are connected to the computer 33 which controls the pulse frequency of the transmitter and serves to record the data from the receiver channels. The computer 33 also serves to process the data for viewing on the display means 65. The computer provides an interface with an operator which allows the operator to control the parameters of data acquisition (for example, transmitter pulse frequency, transmitter pulse magnitude) and allows the operator to control parameters for displaying the results. In the preferred embodiment, the display means is a cathode ray (CRT) monitor 65.

The noise antenna 63 is a single receiving antenna connected to a receiver channel in the receiver 61. The receiver channel which is connected to the noise antenna is referred to as the noise channel.

The method of detecting irregularities on a conductive container of the present continuation-in-part invention will now be described. First, the transmitting antenna 57 is placed on the pipeline jacket 19 so as to be in proximity with the portion of the pipe wall 15 which is to be investigated and so as to enclose an area on the outer surface of the jacket 19. Then, the receiving antenna array 59 is laid on that portion of the jacket 19 which is enclosed by the transmitting antenna 57. The receiving antenna array 59 is positioned within the enclosed area so as to be located primarily within the central portion of the transmitting antenna interior space, wherein a large portion, if not all of receiving antenna array lies within the area of relatively uniform field produced by the induced current. When placed on the pipeline 11, the receiving antenna array 59 forms a matrix having rows of receiving antennas, which extend longitudinally on the pipeline, and columns of receiving antennas, which extend circumferentially around the pipeline (so as to extend around a portion of the circumference). The transmitting antenna and the receiving antenna array are held in place on the pipeline by suitable means (not shown). When positioned on the pipeline, the transmitting antenna and the receiving antenna array are arcuately configured so as to conform to the curvature of the jacket 19. The noise antenna 63 is placed on the pipeline 11 at some distance away from the transmitting antenna 57 and receiving antenna array 59. The noise antenna 63 is located sufficiently far away from the transmitting antenna 57 such that the noise antenna receives an ambient electromagnetic field (ambient noise) which is unaffected by the transmitting antenna electromagnetic field. A typical distance between the transmitting antenna and the noise antenna might be ten to twenty feet. The noise antenna 63 is held onto the pipeline by suitable means (not shown).

After the detection apparatus is set up, the transmitting antenna 57 is provided with an abruptly changing current so as to induce current into the pipe wall 15. In the preferred embodiment, current is induced into the pipe wall as follows: the transmitting antenna 57 is energized by the transmitter 29 for a period of time. As described above, the transmitting antenna is energized for a sufficient period of time such that the magnitude of the current in the transmitting antenna is stabilized to insure no inadvertent eddy currents are induced into the pipeline. As described above, the transmitting antenna is typically energized with one to five amps. However, because the transmitting antenna is physically separate from the receiving antennas, the transmitting antenna can be constructed to handle higher energizing currents wherein a higher signal-to-noise ratio can be achieved. Then, the transmitting antenna 57 is abruptly deenergized by the transmitter 29 by having the magnitude of the current fall rapidly to zero. This abrupt change in the transmitting antenna current induces eddy currents into the pipe wall 15.

As soon as the transmitting antenna 57 is deenergized, the receiver 61 is turned on and all receiving antenna channels are measured simultaneously. The individual receiving antennas detect the presence of and the decay of the induced current and generate respective received signals on the respective receiving antenna channels. The noise antenna 63 detects the ambient electromagnetic noise along the pipeline 11 and generates a noise signal on the noise channel. The noise channel is measured simultaneously with the induced current measurements on the receiving antenna channels.

The received signals, including the noise signal, are amplified and filtered. The received signals and the noise signal are digitized and stored in the computer 33 for processing. Simultaneous measurement can be achieved with a small number of A/D converters servicing a large number of receiving antenna and noise channels, if the sampling rate is sufficiently fast. For example, with induced eddy currents, the time scales of interest are in the millisecond range. An A/D converter operating at 1 MHz could service many receiving antenna and noise channels, with the resulting digitized signals appearing, for all practical purposes, to be simultaneously measured.

Figure 16:
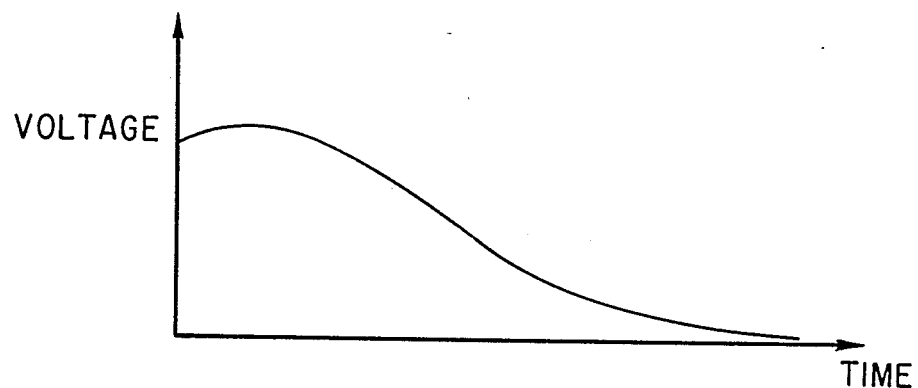
FIG. 16 is a graph showing a response curve obtained with the antenna arrangement of FIG. 9.

The transmitting and receiving procedure is repeated many times with the antennas located in the same position in order to allow stacking of the received signals to increase the signal-to-noise ratio. The received signals are then processed to reduce noise and to prepare the data for display. In FIG. 16, there is shown a graph of a received signal obtained from a detection apparatus using separated transmitting and receiving antennas as shown in FIG. 9. Each digitized received signal is made up of a series of time samples. The individual time samples can be combined into larger time samples for data processing. For example, the time samples measured at or near 5 milliseconds of a received signal can be combined into a larger composite time sample, which encompasses plural time samples and is centered at 5 milliseconds. These composite time samples, which are larger than the actual sampling periods, will be used hereinafter to describe the processing and display of the received signals.

Spatial resolution of the received signals is greatly enhanced by the method of the present continuation-in-part invention because the receiving antenna channels are simultaneously measured. This is because most noise sources (for example power line noise, sferics, motion-induced noise) picked up during TEMP data acquisition are coherent across the receiving antenna array. Thus, for any given time sample, the noise does not affect the induced current as seen by one receiving antenna any more or less than it affects the induced current as seen by the other receiving antennas. Instead, the noise raises or lowers the background (or dc) level of the entire array of received signals for a given time sample.

This increase in spatial resolution is most evident with the analysis of data at a particular sample time. From one time sample to another, resolution (temporal resolution) can be increased by subtracting the noise signal, obtained from the noise antenna 63, from each of the received signals. The noise signal is coherent with the noise present in the receiving antennas because the spatial changes in the noise present at the receiving antenna array and the noise antenna are negligible, and because the noise signal is measured simultaneously with the received signals. Thus, subtraction of the noise signal from each of the received signals decreases the noise content from time sample to time sample.

The next step in processing the received signals is the normalization of the received signals at each time sample. The received signals are normalized to produce a smoothed response representing the unflawed portions of the pipe. This smoothed response is referred to the background response because it provides the background against which pipe wall anomalies are measured. In the case of the monitor 65, the background response provides a uniform background against which pipe wall anomalies can be visually contrasted. The received signals are normalized because unflawed portions of pipelines produce uneven responses across the receiving antenna array 59, making interpretation difficult. Interpretation is made easier by smoothing out the background response of the unflawed portions of the pipe.

Figure 19:
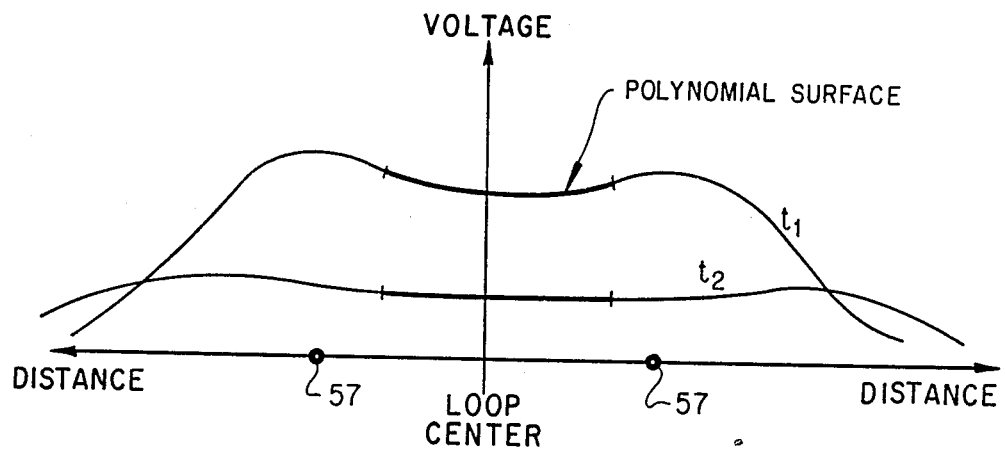
FIG. 19 is a profile of the received signal, at different times, obtained with the antenna arrangement of FIG. 9, with the profile being taken along an imaginary line parallel to the longitudinal axis of the pipeline and through the center of the transmitting antenna.

The background response is, in mathematical terms, a polynomial surface fitted to the measured received signals. In FIG. 19, there is shown a profile of the received signal along the longitudinal direction of the pipeline. The received signal is obtained with the antenna configuration of FIG. 9. Time $t_1$ is earlier than time $t_2$. The polynominal surface for each time (shown as a heavy curve segment) is fitted to the area of a relatively uniform field within the transmitting antenna 57. The polynomial surface is tailored to suit the actual geometry of the antennas and the pipe wall. The background response of the central portion of the transmitting antenna interior space, where the induced current field is relatively uniform, requires a relatively low order polynomial surface. Outside of this central portion, the complexity of the polynomial surface increases. Conventional methods are used to fit the polynomial surface to the measured received signals.

With the received signals normalized, the anomalous areas are expressed in terms of percentage difference from the background response.

Figure 14:
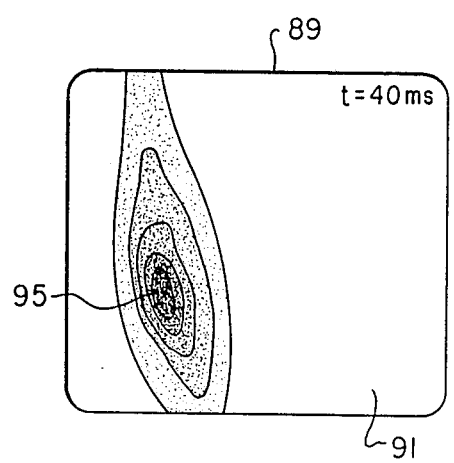

The received signals, having been processed, are now ready for display on the CRT monitor 65, wherein the operator can observe the decay of the induced current. The monitor 65 shows one screen 89 at a time (see for example FIG. 12). Each screen 89 is a two-dimensional display of received signals at a particular time sample. Thus, each screen is like a snapshot, freezing the decay of the induced current at a particular time. For example, in FIG. 14 there is shown the screen displaying all of the received signals measured at 40 ms after the receiver is turned on.

The received signals are displayed on a monitor screen in a convenient spatial configuration to provide spatial correspondence between the receiving antenna array and the display. It thus appears as if the pipe wall is unwrapped for display. To describe the spatial configuration of the received signals on a monitor screen 89, it will be convenient to refer to "upper", "lower", "left", and "right" with reference to the orientation of FIGS. 9, 11–14. Received signals from the upper row of receiving antennas are displayed along the upper part of the screens 89 of FIGS. 11–14; signals from the lower row of receiving antennas are displayed along the lower part of the screens; signals from the left column of receiving antennas are displayed along the left part of the screens; signals from the right column are displayed along the right part of the screens. Received signals from the other receiving antennas are similarly distributed relative to the spatial distribution of their respective receiving antennas. The display shows a two-dimensional planar projection of the received signals from the curved receiving antenna array.

Ideally, there should be a large enough number of individual receiving antennas so that there is a one-to-one correspondence between the receiving antenna 69 and pixels (not shown) on the display screen 89. With such a receiving antenna array, the resolution of each screen is high. A smaller number of receiving antennas could be utilized with interpolation between adjacent receiving antennas to determine what values should be assigned to those pixels that do not correspond with receiving antennas.

A single display screen 89 is created for each time sample. The operator can cause the display 65 to show consecutive screens with consecutive time samples to aid in his interpretation of the data. In this fashion, the operator can watch a "movie" on the display, wherein the received signals change with time.

Figure 11:
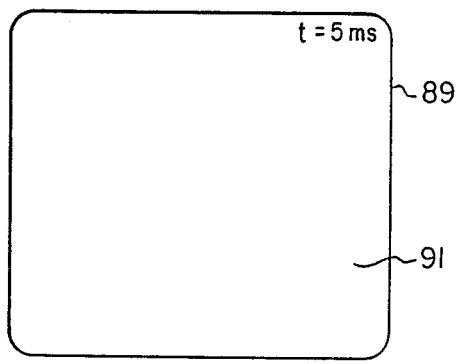
FIGS. 11-14 are schematic diagrams of two dimensional display screens obtained with the detection situation of FIG. 9, showing the thickness of the pipeline wall at different sample times.

An example of a "movie" sequence is shown in FIGS. 11–14. In FIG. 11, the screen 89 obtained from the received signals at 5 ms is shown, in FIG. 12 the screen shows received signals obtained at 10 ms, in FIG. 13 the screen shows received signals obtained at 20 ms, and in FIG. 14, the screen shows received signals obtained at 40 ms. The white background 91 in FIGS. 11–14 represent the background response of the uncorroded areas of the pipe wall, which have a uniform thickness. The darker areas 93,95, which are identified by contour lines and stippling in FIGS. 11–14, represent those areas of the pipe wall which are thinner than the uncorroded areas. The darkest areas are those areas where the pipe wall is the thinnest (where the corrosion is the heaviest).

As described above, at intermediate and late times, thinner (corroded) areas become distinguishable from thicker (uncorroded) areas. Thus, on the screens displaying the intermediate and late time portions of the received signals (FIGS. 12–14) the slightly thinner area 93 becomes discernable from the greatly thinner area 95 by virtue of the lighter stippling. As the operator displays screens in consecutive fashion, the thinner areas first make an appearance on the display (FIG. 12) and then enlarge (FIGS. 13–14) as time progresses. By causing the corrosion patterns on the display to change with time, the corrosion areas are easier to discern by the operator than a static display because the enlargement (or shrinkage) takes advantage of characteristics of human vision, wherein a human is more apt to visually detect a moving or changing object than a stationary object. This feature of causing the corroded areas to move on the display by growing or shrinking allows an operator to detect small or weak areas of corrosion that would otherwise blend into the background response and escape visual detection with static display methods.

Figure 12:
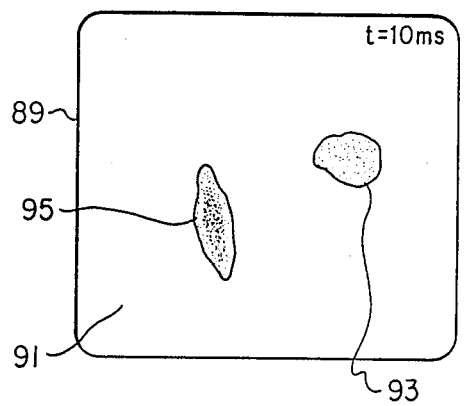
Figure 13:
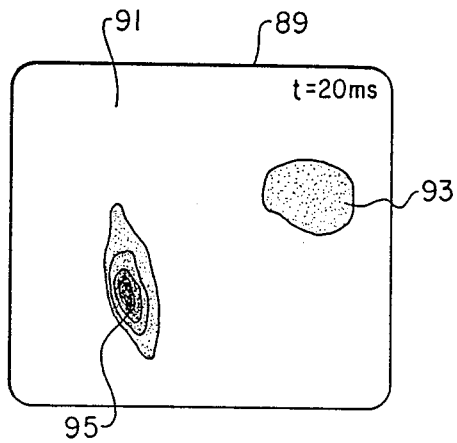

In FIGS. 12 and 13, the area 93 of corrosion appears at 10 ms and 20 ms, and then disappears from the screen at 40 ms. This shows an area 93 of weak corrosion, where the wall loss caused by corrosion is small. To further enhance detection of weak areas, the operator can employ scale stretching. Scale stretching utilizes the full dynamic range of the display equipment 65 by allowing the operator to stretch the scale between the background response and the heaviest corrosion so that it matches the scale of the display. For example, the operator might initially assign the darkest possible stippling to 20% wall loss. If, upon looking at the screen, he sees no areas with the darkest stippling, he can stretch the scale of the received signals so that the darkest stippling now represents 10% wall loss and so on. By calibrating the detection apparatus, quantitative measurements of wall thickness can be made.

The operator can scroll between screens back and forth in time to obtain the optimum screen or sequence of screens. Scrolling to select an optimum screen is useful for quantitative analysis. Screens which are temporally intermediate to actual screens could be synthesized by interpolation between two adjacent screens to enhance the smoothness of the transition from one screen to the next. Because of the fast (generally within 100 ms) decay times of the induced current, the display would not show the screens in real time; instead the operator could adjust the speed of scrolling to a comfortable level. However, the detection apparatus could allow real time processing.

The received signals can be displayed on the monitor in configurations other than contour lines and stippling. For example, a grey scale could be used, where white represents the thickest wall portion and black represents the thinnest wall portion, with various shades of grey representing the intermediate thicknesses. By assigning the average wall thickness an intermediate shade of grey, areas that are thicker and thinner than the average value could be displayed. Thicker areas would have lighter shades of grey while thinner areas would have darker shades of grey. Another alternative configuration is a color scale if a color monitor is used. Red could represent thick areas and violet could represent thin areas, with orange, yellow, green, and blue respectively representing progressively thinner areas.

An alternative method to perform a quantitative analysis of the corroded areas is to examine the entire transient decay curve for one or more received signals from the corroded area, using the methods described above to analyze the decay of induced current. The noise signal is subtracted from the received signals of interest to reduce noise over the length of the time sample. The intermediate and late time portions of each received signal is compared to the intermediate and late time portions of a reference received signal, which has been obtained from a reference pipe wall of known thickness. Alternatively, the received signal can be compared to other received signals which have been obtained from pipe wall portions which are free of irregularities. The detection apparatus 55 can be calibrated by determining the wall thickness for a small number of received signals in this manner. These calibrated reference signals can then be used in comparisons with unknown received signals.

Although the transmitting antenna has been described as being generally rectangular, other shapes or configurations could be used which produce a relatively uniform transmitted electromagnetic field with respect to the receiving antenna array. For example, the transmitting antenna could circular in shape.

Figure 10:
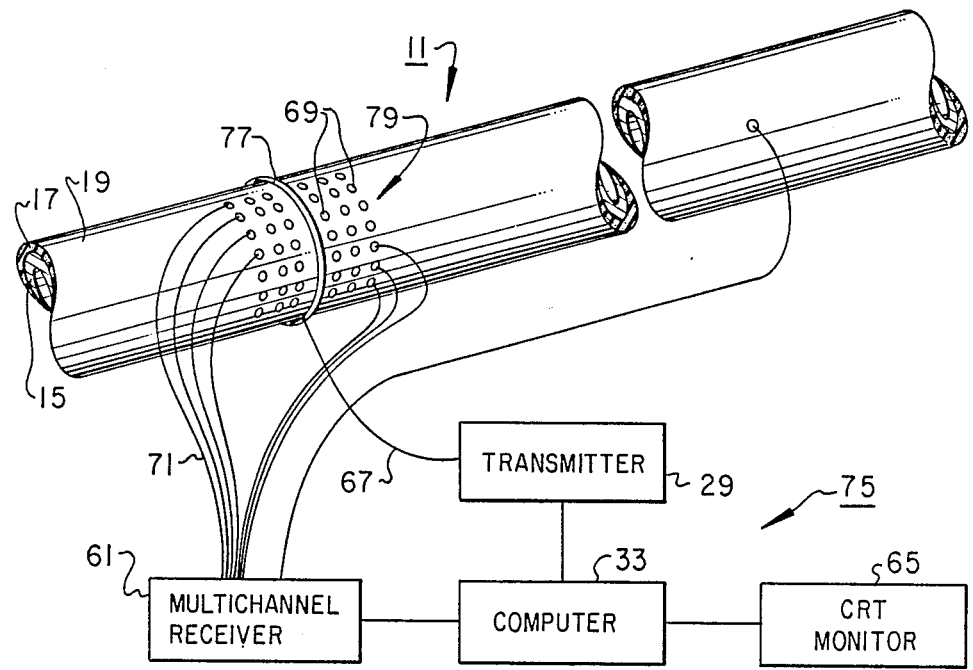
FIG. 10 is a schematic diagram showing another embodiment of a typical situation in which the method of the present continuation-in-part invention can be practiced.

In FIG. 10, there is shown a schematic diagram showing another situation for practicing the method of the present continuation-in-part invention. The detecting apparatus 75 shown in FIG. 10 is the same as the detecting apparatus 55 of FIG. 9, with the exception of the transmitting antenna means 77 and the receiving antenna means 79.

The transmitting antenna means includes a loop antenna 77. The transmitting loop antenna 77 is made up of one or more turns of conductive wire which is either preformed to conform to the pipeline 11 or wrapped around the pipeline. The transmitting loop antenna 77 encompasses an interior space; the pipeline 11 is located within the interior space of the antenna 77. The transmitting loop antenna 77 encircles the circumference of the pipeline 11. The antenna is placed on the jacket 19 so as to be in proximity with the pipe wall. The transmitting antenna need not be a closed loop antenna; it can be any configuration that induces current to flow in the pipe wall 15. The receiving antenna means 79 includes multiple individual receiving antennas 69. The receiving antennas 69 are similar to the receiving antennas described in relation to FIG. 9. The receiving antennas 69 are placed around the pipe in sets of parallel rings located laterally of the transmitting antenna. Thus, a first set of receiving antennas lies adjacent to one side of the transmitting antenna, followed by a second set, a third set, and so on. The sets of receiving antennas are spaced longitudinally along the pipe. A fourth set of receiving antennas lies adjacent to the other side of the transmitting antenna, followed by a fifth set, a sixth set, and so on. Each set includes a plurality of receiving antennas arranged in a ring that encompasses the pipe. The receiving antennas 69 are oriented with the longitudinal axis of the respective core means normal to the pipe wall 15 immediately adjacent to the receiving antennas. The receiving antennas 69 in all of the sets are spatially distributed in an arrangement having rows, which extend longitudinally along the pipe, and columns, each column being a set of receiving antennas. This array of receiving antennas corresponds to a two-dimensional matrix that can be displayed on the monitor 65. The receiving antenna array is electronically divided between two adjacent rows and electronically unwrapped for viewing on the display. The noise antenna 63 is placed on the pipeline at some distance away from the transmitting antenna 77 as described above.

Figure 17:
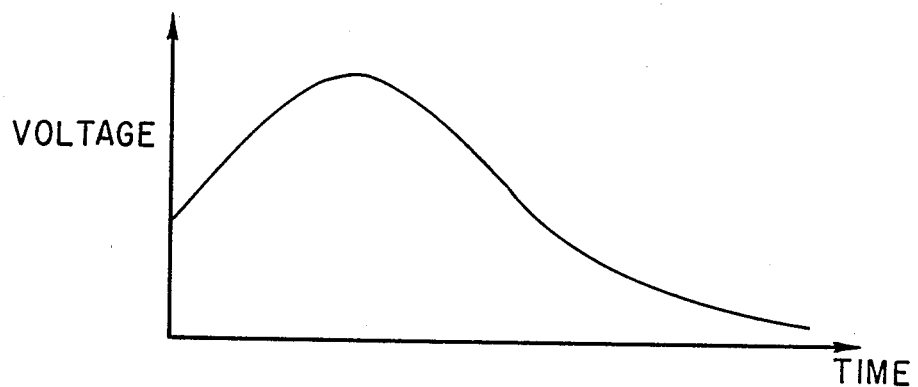
FIG. 17 is a graph showing a response curve obtained with the antenna arrangement of FIG. 10.
Figure 20:
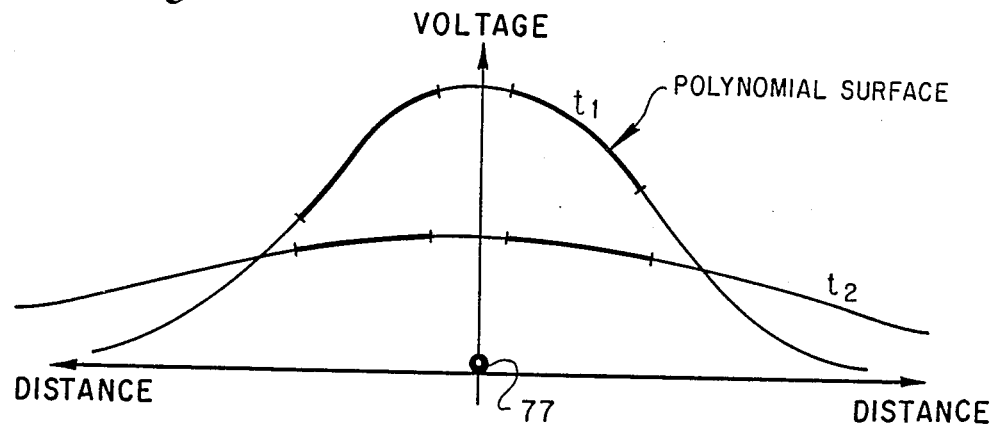
FIG. 20 is a profile of the received signal, at different times, obtained with the antenna arrangement of FIG. 10, with the profile being taken along an imaginary line parallel to the longitudinal axis of the pipeline.

The data acquisition, data processing, display and interpretation steps for the detection apparatus of FIG. 10 are similar to the steps described above in regard to FIG. 9. The background response is defined in the same manner as the background response of the antenna configuration of FIG. 9. The background response is uniform in a circumferential direction, but is non-uniform in a longitudinal direction. The induced currents flow circumferentially around the pipe, diffusing radially inward and broadening longitudinally out from the transmitting antenna 77. FIG. 17 shows a received signal as detected by one of the receiving antennas 69. FIG. 20 shows a profile of the received signal along the longitudinal direction of the pipeline (where time $t_1$ is earlier than time $t_2$). The polynomial surface for each time (shown as a heavy curve segment) is fitted to the receiver antenna array area in both a circumferential direction and a longitudinal direction (see FIG. 20).

Figure 15:
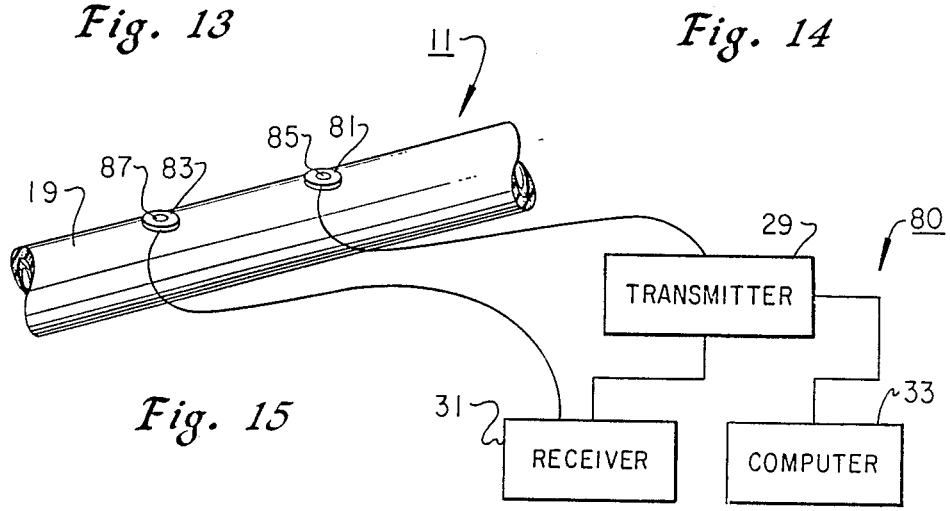
FIG. 15 is a schematic diagram showing another embodiment of a typical situation in which the method of the present continuation-in-part invention can be practiced.

The method of detecting wall loss can also be practiced with the detecting apparatus 80 shown in FIG. 15. The detecting apparatus 80 includes the transmitter 29, the receiver 33, and the computer 33, all of which were described above, along with a transmitting antenna 81 and a receiving antenna 83. The transmitting antenna 81 is made up of a coil wound onto a nonmagnetic and nonconductive core means 85. The receiving antenna is also made up of a coil wound onto a similar type of core means 87. Unlike the coincident loop arrangement shown in FIG. 3, the transmitting and receiving antennas of FIG. 15 are wound on two distinct core means, allowing for the physical separation of the antennas. The respective core means have respective longitudinal axes. The respective coils are wound circumferentially around the respective core means 85,87. The transmitting antenna 81 and the receiving antenna 83 are placed on the metal jacket 19. The antennas 81, 83 need not be coplanar with each other. The insulation and the metal jacket are interposed between the antennas and the pipe wall. The transmitting and receiving antennas 81, 83 are separated from each other so as to form a loop-loop configuration.

Figure 18:
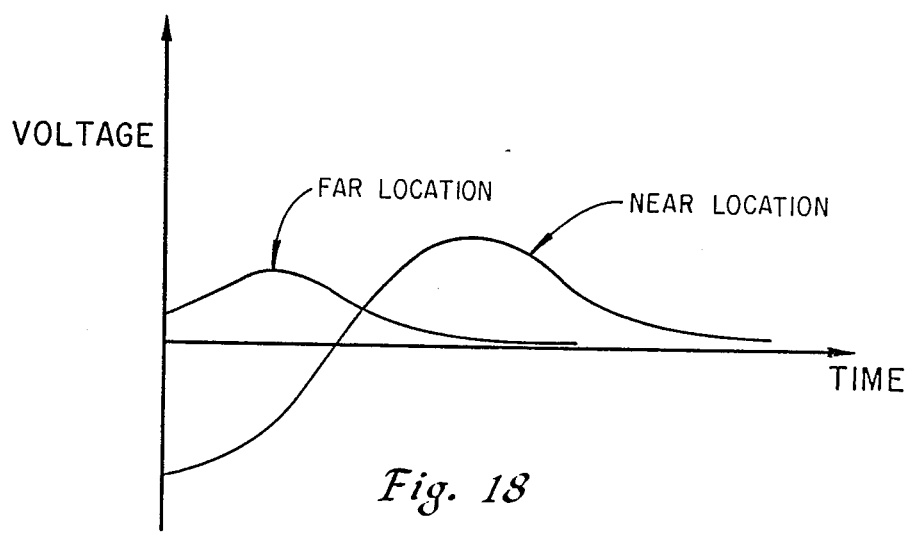
FIG. 18 is a graph showing response curves obtained with the antenna arrangement of FIG. 15.
Figure 21:
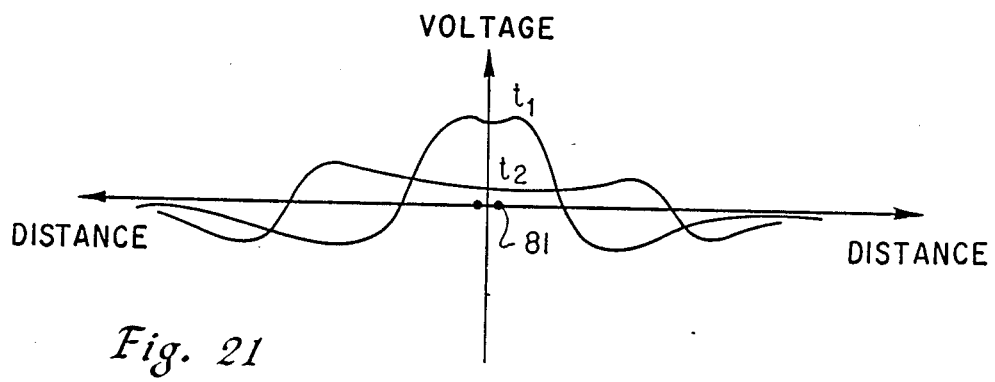
FIG. 21 is a profile of the received signal, at different times, obtained with the antenna arrangement of FIG. 15, with the profile being taken along an imaginary line parallel to the longitudinal axis of the pipeline.

In FIG. 18, there is shown a graph of received signals obtained with the detection apparatus 80 of FIG. 15 with the receiving antenna 83 located at near and far locations from the transmitting antenna. The intermediate and late time ranges of the received signal, and in particular the portion of the received signal after the induced current crosses over zero volts, is examined and compared to reference received signals obtained from reference pipelines having known wall thicknesses. As described above, the thinner pipe walls will have induced currents that decay earlier and faster than the thicker pipe walls. Alternatively, the received signal can be compared to other received signals, which have been obtained from pipe wall portions which are free of irregularities. FIG. 21 shows a profile of the received signal along the longitudinal direction of the pipeline with the transmitting antenna held stationary and the receiving antenna moved along the pipeline to plural locations.

The loop-loop configuration provides some flexibility over the coincidental configuration shown in FIG. 3. With the loop-loop configuration, the separated antennas can be positioned in accordance with pipeline geometrical considerations. Furthermore, the receiving antenna receives only a portion of the induced current, which portion has directional characteristics instead of the omnidirectional characteristics of the induced current received by the coincidental receiving antenna. These directional characteristics of the induced current can be utilized in detecting directional anomalies such as cracks in the pipe wall. Wall cracks are more easily detected by inducing current to flow perpendicularly across the cracks rather than parallel thereto.

Although this invention has been described with a certain degree of particularity, it is understood that the present disclosure is made only by way of example and that numerous changes in the details of construction and the combination and arrangement of parts may be resorted to without departing from the spirit and the scope of the invention, reference being had for the latter purpose to the appended claims.

I claim:

1. A method of detecting irregularities on electrically conductive walls of container means, comprising the steps of:
    (a) providing transmitting antenna means and transmitter means connected with said transmitting antenna means;
    (b) providing receiving antenna means and receiver means, said receiving antenna means comprising many receiving antennas, said receiver means being connected with each of said receiving antennas;
    (c) providing a two-dimensional display means for displaying the received signals;
    (d) placing said transmitting antenna means in proximity to that portion of the container means wall which is to be investigated for irregularities;
    (e) placing said receiving antenna means in proximity to that portion of the container means wall which is to be investigated for irregularities, said receiving antenna means being placed near said transmitting antenna means, said individual receiving antennas being distributed over said container means wall portion in a predetermined spatial relationship with one another;
    (f) providing an abruptly changing current to said transmitting antenna means from said transmitter means so as to induce current into the investigated container means wall portion;
    (g) detecting the presence of and the decay of said induced current in said investigated container means wall portion with said receiving antennas and said receiver means to produce many received signals, said many received signals being obtained simultaneously by said receiving antennas and said receiver means;
    (h) dividing the received signals into samples of time, such that the respective samples of time of each received signal correspond to respective samples of time of the other received signals;
    (i) creating a two-dimensional display on said display means for a sample of time by displaying the respective corresponding time sample of each of the received signals in a spatial arrangement on said display means that corresponds to the spatial arrangement of said receiving antennas on said container means wall portion, wherein for each sample of time there is a corresponding two-dimensional display.

2. The method of claim 1, wherein:
    (a) said transmitting antenna means comprises a loop antenna, said transmitting loop antenna encompassing an interior space, said interior space for receiving said receiving antenna array;
    (b) said transmitting loop antenna is placed over said container means wall portion;
    (c) said receiving antenna means is placed within the interior space of said transmitting loop antenna.

3. The method of claim 2, further comprising the steps of:
    (a) providing noise antenna means separate from said transmitting antenna means and said receiving antenna means, said noise antenna means being connected with said receiver means;
    (b) placing said noise antenna means along said container means wall, said noise antenna means being placed at a distance from said transmitting antenna means such that said noise antenna means is unaffected by the transmitting antenna means, said noise antenna producing a noise signal;
    (c) subtracting the noise signal received by said noise antenna means from each of the received signals produced by said receiving antennas and said receiver means.

4. The method of claim 3, further comprising the step of displaying on said display means said two-dimensional displays in a consecutive temporal arrangement in order to allow the change in time between said display to provide changes in contrast between areas having different wall thickness.

5. The method of claim 2 wherein said transmitting loop antenna is geometrically configured so as to produce an induced current which produces an electromagnetic field that is relatively uniform over a portion of the interior space of said transmitting loop antenna.

6. The method of claim 1 wherein:
   (a) said transmitting antenna means comprises a loop antenna, said transmitting loop antenna encompassing an interior space;
   (b) said transmitting loop antenna is placed around the container means wall portion such that said container means wall portion is located within said interior space of said transmitting loop antenna;
   (c) said receiving antenna means is placed laterally of said transmitting loop antenna.

7. The method of 6 wherein said receiving antennas are arranged into plural sets with each set comprising plural receiving antennas positioned in an arrangement such that the respective set encompasses an interior space, each of said sets being placed around said container means wall portion such that said container means wall portion is located within said interior space of each set.

8. The method of claim 7, further comprising the steps of:
   (a) providing noise antenna means separate from said transmitting antenna means and said receiving antenna means, said noise antenna means being connected with said receiver means;
   (b) placing said noise antenna means along said container means wall, said noise antenna means being placed at a distance from said transmitting antenna means such that said noise antenna means is unaffected by the transmitting antenna means, said noise antenna producing a noise signal;
   (c) subtracting the noise signal received by said noise antenna means from each of the received signals produced by said receiving antennas and said receiver means.

9. The method of claim 8, further comprising the step of displaying on said display means said two-dimensional displays in a consecutive temporal arrangement in order to allow the change in time between said display to provide changes in contrast between areas having different wall thickness.

10. The method of claim 1, further comprising the step of displaying on said display means said two-dimensional displays in a consecutive temporal arrangement in order to allow the change in time between said display to provide changes in contrast between areas having different wall thickness.

11. The method of claim 1 wherein there are provided at least 20 receiving antennas which are placed in proximity to the container means well portion.

12. The method of claim 1 wherein said container means comprises a pipeline, wherein said transmitting antenna means and said receiving antenna means are placed in proximity to a portion of said pipeline.

13. The method of claim 1 further comprising the step of normalizing said received signals to produce a uniform background response representing unflawed portions of said container means wall portion.

14. The method of claim 1 wherein said transmitting antenna means is provided with an abruptly changing current by energizing said transmitting antenna means for a sufficient period of time to stabilize the magnitude of the current in said transmitting antenna means, and then abruptly deenergizing said transmitting antenna.

15. A method of detecting wall thickness on walls of container means, said walls being electrically conductive, comprising the steps of:
   (a) providing transmitting antenna means and transmitter means connected with said transmitting antenna means;
   (b) providing receiving antenna means and receiver means, said receiving antenna means comprising many receiving antennas, said receiver means being connected with each of said receiving antennas;
   (c) providing a two-dimensional display means for displaying the received signals;
   (d) placing said transmitting antenna means in proximity to that portion of the container means wall which is to be investigated for irregularities;
   (e) placing said receiving antenna means in proximity to that portion of the container means wall which is to be investigated for irregularities, said receiving antenna means being placed near said transmitting antenna means, said individual receiving antenna means being distributed over said container means wall portion in a predetermined spatial relationship with one another.
   (f) providing an abruptly changing current to said transmitting antenna means from said transmitter means so as to induce current into the investigated container means wall portion;
   (g) detecting the presence of and the decay of said induced current in said investigated container means wall portion with said receiving antennas and said receiver means to produce many received signals, said many received signals being obtained simultaneously by said receiving antennas and said receiver means;
   (h) dividing the received signals into samples of time, such that the respective samples of time of each received signal correspond to respective samples of time of the other received signals;
   (i) normalizing said received signals to produce a uniform background response representing unflawed portions of said container means wall portion;
   (j) creating a two-dimensional display on said display means for a sample be of time samples of each of the received signals in a spatial arrangement on said display means that corresponds to the spatial arrangement of said receiving antennas on said container means wall portion, wherein for each sample of time there is a corresponding two-dimensional display;
   (k) comparing the decays of said received signals to the decay of a reference signal obtained from a reference container means wall portion of known thickness.

16. The method of claim 15, further comprising the steps of:
   (a) providing noise antenna means separate from said transmitting antenna means and said receiving antenna means, said noise antenna means being connected with said receiver means;
   (b) placing said noise antenna means along said container means wall, said noise antenna means being placed at a distance from said transmitting antenna means such that said noise antenna mean is unaffected by the transmitting antenna means, said noise antenna producing a noise signal;

(c) subtracting the noise signal received by said noise antenna means from each of the received signals produced by said receiving antennas and said receiver means.

17. The method of claim 16, further comprising the step of displaying on said display means said two-dimensional displays in a consecutive temporal arrangement in order to allow the change in time between said display to provide changes in contrast between areas having different wall thickness.

18. The method of claim 15, further comprising the steps of displaying on said display means said two-dimensional displays in a consecutive temporal arrangement in order to allow the change in time between said display to provide changes in contrast between areas having different wall thickness.

19. A method of detecting wall thickness on walls of container means, said walls being electrically conductive, comprising the steps of:
 (a) providing transmitting antenna means and transmitter means connected with said transmitting antenna means;
 (b) providing receiving antenna means and receiver means, said receiving antenna means comprising many receiving antennas, said receiver means being connected with each of said receiving antennas;
 (c) providing a two-dimensional display means for displaying the received signals;
 (d) placing said transmitting antenna means in proximity to that portion of the container means wall which is to be investigated for irregularities;
 (e) placing said receiving antenna means in proximity to that portion of the container means wall which is to be investigated for irregularities, said receiving antenna means being placed near said transmitting antenna means, said individual receiving antenna means being distributed over said container means wall portion in a predetermined spatial relationship with one another;
 (f) providing an abruptly changing current to said transmitting antenna means from said transmitter means so as to induce current into the investigated container means wall portion;
 (g) detecting the presence of and the decay of said induced current in said investigated container means wall portion with said receiving antennas and said receiver means to produce many received signals, said many received signals being obtained simultaneously by said receiving antennas and said receiver means;
 (h) dividing the received signals into samples of time, such that the respective samples of time of each received signal correspond to respective samples of time of the other received signals;
 (i) normalizing said received signals to produce a uniform background response representing unflawed portions of said container means wall portion;
 (j) creating a two-dimensional display on said display means for a sample of time by displaying the respective corresponding time sample of each of the received signals in a spatial arrangement on said display means that corresponds to the spatial arrangement of said receiving antennas on said container means wall portion, wherein for each sample of time there is a corresponding two-dimensional display;
 (k) comparing the decays of said received signals to the decay of a reference signal obtained from a container means wall portion which is free of irregularities.

20. The method of claim 19, further comprising the steps of:
 (a) providing noise antenna means separate from said transmitting antenna means and said receiving antenna means, said noise antenna means being connected with said receiver means;
 (b) placing said noise antenna means along said container means wall, said noise antenna means being placed at a distance from said transmitting antenna means such that said noise antenna means is unaffected by the transmitting antenna means, said noise antenna producing a noise signal;
 (c) subtracting the noise signal received by said noise antenna means from each of the received signals produced by said receiving antennas and said receiver means.

21. The method of claim 20, further comprising the step of displaying on said display means said two-dimensional displays in a consecutive temporal arrangement in order to allow the change in time between said display to provide changes in contrast between areas having different wall thickness.

22. The method of claim 19, further comprising the step of displaying on said display means said two-dimensional displays in a consecutive temporal arrangement in order to allow the change in time between said display to provide changes in contrast between areas having different wall thickness.

23. A method of detecting irregularities on electrically conductive walls of container means, comprising the steps of:
 (a) providing transmitting antenna means and transmitter means connected with said transmitting antenna means;
 (b) providing receiving antenna means and receiver means, said receiving antenna means comprising plural receiving antennas, said receiver means being connected with each of said receiving antennas;
 (c) placing said transmitting antenna means in proximity to that portion of the container means wall which is to be investigated for irregularities;
 (d) placing said receiving antenna means in proximity to that portion of the container means wall which is to be investigated for irregularities, said receiving antenna means being placed near said transmitting antenna means, said individual receiving antennas being distributed over said container means wall portion in a predetermined spatial relationship with one another;
 (e) providing an abruptly changing current to said transmitting antenna means from said transmitter means so as to induce current into the investigated container means wall portion;
 (f) detecting the presence of and the decay of said induced current in said investigated container means wall portion with said receiving antennas and said receiver means to produce many received signals, said plural received signals being obtained simultaneously by said receiving antennas and said receiver means, each of said received signals having intermediate and late time ranges;

(g) examining said received signal intermediate and late time ranges to determine the decay of said received signal, and comparing the decays of the respective received signals to the decay of a reference signal obtained from a reference container means wall portion of known thickness, wherein said received signal decays from said investigated container means wall portion gives an indication of the thickness of the investigated container means wall portion and the presence or absence of irregularities on the investigated container means wall portion can be determined;

(h) providing noise antenna means separate from said transmitting antenna means and said receiving antenna means, said noise antenna means being connected with said receiver means;

(i) placing said noise antenna means along said container means wall, said noise antenna means being placed at a distance from said transmitting antenna means such that said noise antenna means is unaffected by the transmitting antenna means, said noise antenna producing a noise signal;

(j) subtracting the noise signal received by said noise antenna means from each of the received signals produced by said receiving antennas and said receiver means;

(k) providing a two-dimensional display means for displaying the received signals;

(l) dividing the received signals into samples of time, such that the respective samples of time of each received signal correspond to respective samples of time of the other received signals;

(m) creating a two-dimensional display on said display means for a sample of time by displaying the respective corresponding time sample of each of the received signals in a spatial arrangement on said display means that corresponds to the spatial arrangement of said receiving antennas on said container means wall portion, wherein for each sample of time there is a corresponding two-dimensional display;

(n) displaying on said display means said two-dimensional displays in a consecutive temporal arrangement in order to allow the change in time between said displays to provide changes in contrast between areas having different wall thickness.

24. A method of detecting irregularities on electrically conductive walls of container means, comprising the steps of:

(a) providing transmitting antenna means and transmitter means connected with said transmitting antenna means;

(b) providing receiving antenna means and receiver means, said receiving antenna means comprising plural receiving antennas, said receiver means being connected with each of said receiving antennas;

(c) placing said transmitting antenna means in proximity to that portion of the container means wall which is to be investigated for irregularities;

(d) placing said receiving antenna means in proximity to that portion of the container means wall which is to be investigated for irregularities, said receiving antenna means being placed near said transmitting antenna means, said individual receiving antennas being distributed over said container means wall portion in a predetermined spatial relationship with one another;

(e) providing an abruptly changing current to said transmitting antenna means from said transmitter means so as to induce current into the investigated container means wall portion;

(f) detecting the presence of and the decay of said induced current in said investigated container means wall portion with said receiving antennas and said receiver means to produce many received signals, said plural received signals being obtained simultaneously by said receiving antennas and said receiver means, each of said received signals having intermediate and late time ranges;

(g) examining said received signal intermediate and late time ranges to determine the decay of said received signal, and comparing the decays of the respective received signals to the decay of a reference signal obtained from a reference container means wall portion of known thickness, wherein said received signal decays from said investigated container means wall portion gives an indication of the thickness of the investigated container means wall portion and the presence or absence of irregularities on the investigated container means wall portion can be determined;

(h) providing a two-dimensional display means for displaying the received signals;

(i) dividing the received signals into samples of time, such that the respective samples of time of each received signal correspond to respective samples of time of the other received signals;

(j) creating a two-dimensional display on said display means for a sample of time by displaying the respective corresponding time sample of each of the received signals in a spatial arrangement on said display means that corresponds to the spatial arrangement of said receiving antennas on said container means wall portion, wherein for each sample of time there is a corresponding two-dimensional display;

(k) displaying on said display means said two-dimensional displays in a consecutive temporal arrangement in order to allow the change in time between said displays to provide changes in contrast between areas having different wall thickness.

* * * * *

UNITED STATES PATENT AND TRADEMARK OFFICE
CERTIFICATE OF CORRECTION

PATENT NO. : 4,929,898

DATED : May 29, 1990

INVENTOR(S) : Brian R. Spies

It is certified that error appears in the above-identified patent and that said Letters Patent is hereby corrected as shown below:

Column 21, line 56, change "well" to read ---wall---.

Column 22, line 48, after the first "sample" delete "be"; after "time" insert ---by displaying the respective corresponding time---; change "samples" to read ---sample---.

Signed and Sealed this

First Day of October, 1991

Attest:

Attesting Officer

HARRY F. MANBECK, JR.

Commissioner of Patents and Trademarks